(12) United States Patent
Sakaki

(10) Patent No.: US 11,478,564 B2
(45) Date of Patent: Oct. 25, 2022

(54) DECONTAMINATION DEVICE AND DECONTAMINATION METHOD EMPLOYING SAID DECONTAMINATION DEVICE

(71) Applicant: SD BIOSYSTEM CO., LTD, Tokyo (JP)

(72) Inventor: Akio Sakaki, Tokyo (JP)

(73) Assignee: SD BIOSYSTEM CO., LTD, Tokyo (JP)

( * ) Notice: Subject to any disclaimer, the term of this patent is extended or adjusted under 35 U.S.C. 154(b) by 5 days.

(21) Appl. No.: 16/335,336

(22) PCT Filed: Jan. 30, 2018

(86) PCT No.: PCT/JP2018/002951
§ 371 (c)(1),
(2) Date: Mar. 21, 2019

(87) PCT Pub. No.: WO2018/143186
PCT Pub. Date: Aug. 9, 2018

(65) Prior Publication Data
US 2019/0275185 A1  Sep. 12, 2019

(30) Foreign Application Priority Data

Jan. 31, 2017  (JP) .............................. JP2017-015403

(51) Int. Cl.
*A61L 2/26* (2006.01)
*A61L 2/22* (2006.01)
(Continued)

(52) U.S. Cl.
CPC ....... *A61L 2/26* (2013.01); *A61L 2/18* (2013.01); *A61L 2/22* (2013.01); *A61L 2/24* (2013.01); *A61L 9/14* (2013.01); *A61L 2202/15* (2013.01)

(58) Field of Classification Search
CPC ..... A61L 2/26; A61L 2/24; A61L 2/18; A61L 2/22; A61L 9/14; A61L 2202/15;
(Continued)

(56) References Cited

U.S. PATENT DOCUMENTS 6,007,780 A * 12/1999 Heredia ............... A61L 2/24
422/105
6,076,739 A * 6/2000 Littleford ............ F24F 3/044
236/44 R
(Continued)

FOREIGN PATENT DOCUMENTS

CN  103619361 A   3/2014
JP  2011147673 A  8/2011
(Continued)

OTHER PUBLICATIONS

International Search Report dated Feb. 27, 2018 for PCT/JP2018/002951 to SD Biosystem Co.,Ltd filed Jan. 30, 2018.

*Primary Examiner* — Regina M Yoo
(74) *Attorney, Agent, or Firm* — Vorys, Sater, Seymour and Pease LLP

(57) ABSTRACT

Decontamination device and method for sterilizing an inside of facility or an inside of a device installed in the facility in which cells, tissues, culture media, sterile reagents, microorganisms or the like are handled or cultured, including: dry fog generating machine, installed in decontamination area, for converting peracetic acid mixed solution containing low-concentration peracetic acid into dry fog and spraying the dry fog into the decontamination area; humidity sensor, installed in decontamination area, for measuring humidity in decontamination area; gas recovery machine, installed in the above decontamination area, for recovering gas in decontamination area; and control device for controlling spraying from dry fog generating machine and gas recovery operation by the gas recovery machine based on information from the (Continued)

above humidity sensor, a main control and monitoring device, installed outside the above decontamination area, for controlling the control devices of one or more of the above decontamination devices.

8 Claims, 8 Drawing Sheets

(51) Int. Cl.
*A61L 9/14* (2006.01)
*A61L 2/24* (2006.01)
*A61L 2/18* (2006.01)

(58) Field of Classification Search
CPC .......... A61L 2209/135; A61L 2202/13; A61L 2202/25; A61L 2209/111; A61L 2202/11; A61L 2202/14
See application file for complete search history.

(56) References Cited

U.S. PATENT DOCUMENTS

| | | | |
|---|---|---|---|
| 2011/0091354 A1* | 4/2011 | Schwartz | A61L 2/20 422/28 |
| 2012/0275953 A1 | 11/2012 | Lukasik et al. | |
| 2012/0288406 A1 | 11/2012 | Iwashita et al. | |
| 2013/0183794 A1 | 7/2013 | Xiong et al. | |
| 2014/0205500 A1 | 7/2014 | Sakaki | |
| 2015/0064066 A1* | 3/2015 | Schwartz | A61L 2/20 422/29 |
| 2016/0022852 A1 | 1/2016 | Sakaki | |
| 2019/0209806 A1* | 7/2019 | Allen | G05B 15/02 |

FOREIGN PATENT DOCUMENTS

| | | |
|---|---|---|
| JP | 2014140481 A | 8/2014 |
| JP | 2015-211772 A | 11/2015 |
| JP | 2016022144 A | 2/2016 |

* cited by examiner

FIG. 2A

|     | Procedure |
| --- | --- |
| (a) | Set a reference temperature ($T_1$) and a reference humidity ($H_1$), and determine an effective decontamination period ($t_1$) at a set decontamination humidity (H) by measuring it a plurality of times. |
| (b) | Obtain an amount of medicament to be sprayed based on the saturated vapor amount $a(T_1)$ at the reference temperature ($T_1$) and the ratio between the reference humidity ($H_1$) and the extent to which the humidity can be increased. |
| (c) | Obtain an amount of medicament to be sprayed based on the saturated vapor amount $a(T_0)$ at an initial temperature ($T_0$) and the ratio between an initial humidity ($H_0$) and the extent to which the humidity can be increased. |
| (d) | Obtain the ratio between the amount of medicament at the reference temperature and humidity and the amount of medicament at the initial temperature and humidity based on the ratio between (b) and (c). |
| (e) | Humidify with the medicament until the humidity increases from the initial temperature and humidity of (c) to a set decontamination humidity (H), and determine an effective decontamination period by measuring it a plurality of times. |
| (f) | Multiply the effective decontamination period ($t_1$) from (a) by the ratio of medicament from (d). |
| (g) | Obtain a temperature coefficient ($\alpha$) and a humidity coefficient ($\beta$) in consideration of weights for temperature and humidity so that (f)≈(e) and multiply them by respective coefficients. |
| (h) | Add time ($t_2$) for compensating an error of the hygrometer sensor to (g). |
| (i) | An arbitrary decontamination period ($t_d$) can be obtained by inputting the initial temperature ($T_0$) and the initial humidity ($H_0$) into the following equation:<br>$t_d = \alpha \times a(T_1)/a(T_0) \times \beta \times H_1/(H-H_0) \times t_1 + t_2$ |

FIG. 2B

| Decontamination period | $(t_d)$ |
|---|---|
| Effective decontamination period at reference temperature and humidity | $(t_1)$ |
| Time for compensating error of temperature-humidity sensor | $(t_2)$ |
| Initial temperature in decontamination area | $(T_0)$ |
| Initial humidity in decontamination area | $(H_0)$ |
| Reference temperature | $(T_1)$ |
| Reference humidity | $(H_1)$ |
| Set decontamination humidity | $(H)$ |
| Saturated vapor amount at initial temperature | $a(T_0)$ |
| Saturated vapor amount at reference temperature | $a(T_1)$ |
| Temperature coefficient | $(\alpha)$ |
| Humidity coefficient | $(\beta)$ |

Cyclic decontamination method (12 hours)

Dry fog (1 hour)

Commercially-available spray    (1 hour)

DECONTAMINATION DEVICE AND DECONTAMINATION METHOD EMPLOYING SAID DECONTAMINATION DEVICE

CROSS-REFERENCE TO RELATED APPLICATIONS

This is a § 371 National Stage Application of International Application No. PCT/JP2018/002951 filed on Jan. 30, 2018, claiming the priority of Japanese Patent Application No. 2017-015403 filed on Jan. 31, 2017.

TECHNICAL FIELD

This invention relates to a decontamination device for decontaminating a sterile manufacturing facility, a regenerative medicine products manufacturing facility or the like and machines and devices in such a facility, and a decontamination method employing the decontamination device.

BACKGROUND ART

Currently, periodic or daily sterilization operations (space decontamination operations) performed in sterile manufacturing facilities of pharmaceutical companies, sterile inspection rooms, regenerative medicine products manufacturing facilities, sterile experimental animal breeding rooms, operating rooms, food manufacturing facilities or pathogenic microorganisms handling and management facilities and in the devices installed in such facilities, in which cells, tissues, culture media, sterile reagents, microorganisms or the like are handled or cultured, are important for prevention of infection and contamination caused by microorganisms, safety and quality stability of medicaments and products manufactured, data reliability and safety of operators, and there is an increasing demand for a higher level of decontamination in recent years.

Even in Japanese Pharmacopoeia, decontamination methods are newly added to sterilization and disinfection methods in the 17th revised edition of Pharmacopoeia put into effect in April 2016. The decontamination agents for the decontamination methods described in Japanese Pharmacopoeia are formaldehyde, hydrogen peroxide and peracetic acid. In addition to these medicaments, a space decontamination method using chlorine dioxide is currently implemented.

However, space decontamination using these medicaments has various problems including carcinogenicity, harmfulness to humans, residual toxicity, corrosivity, solubility in liquids, adsorptivity and permeability into some basic materials such as celluloses and resins and reemission therefrom, and odor. These medicaments can reduce the number of microorganisms and sterilize spaces and are therefore effective, but are harmful to humans and corrode metals and devices. The current situation is that these advantages and disadvantages are balanced as much as possible to implement a more effective decontamination method. Also, when such space decontamination is carried out, the machines and devices in the decontamination area are entirely covered with vinyl sheets or the like to protect them from getting wet and corroded.

Under such circumstances, the peracetic acid (peracetic acid mixed solution) has been confirmed to be safe to humans at low concentrations, and has strong oxidation power. To reduce protection of devices in decontamination using peracetic acid, the devices must never get wet from the beginning to the end of the decontamination and the entire process must be completed in a dry state.

When the surface of a metal that rusts easily get wet with a peracetic acid mixed agent sprayed, ionization occurs and the reaction between free electrons of oxygen and metal ions induces corrosion (wet corrosion). On the other hand, in dry corrosion, which is a phenomenon in which a metal wears without moisture, the effect of corrosion can be reduced because the reaction speed is extremely slow at a temperature around room temperature. Then, to prevent the treatment targets from getting wet, it is important to spray the peracetic acid mixed agent as a mist of fine particles. The fine particles are in a physically strong state and have the property of being less likely to deform and bouncing without change when colliding with walls. This is called dry fog consisting of particles of 30 µm or smaller and known as fog that does not wet anything it touches.

One device that uses such a peracetic acid mixed agent as dry fog is disclosed in Patent Document 1. This is a decontamination device that includes a plurality of sprayer units including one or more sprayers for atomizing a peracetic acid disinfectant by blowing air to release liquid droplets, one or more temperature-humidity sensors, and a primary controller for starting or stopping the sprayers based on humidities detected by the temperature-humidity sensors during decontamination treatment, a repeater that communicates with the primary controllers, and a main controller that communicates with the repeater and can grasp and control conditions of at least one of the plurality of sprayer units. Document 1 JP-B-5969404. Paragraph discloses that, according to the present invention, even if the supply voltage and the frequency change in a local manner in the above-described sprayer, it is possible to stably generate a droplet having a very small diameter (micron-size) by adjusting the amount of the air and the amount of the drug. The center diameter of this droplet is preferably 3 to 15 µm, more preferably 3 to 10 µm. Such very small droplets, also referred to as dry fog, have characteristics such as non-wetting fog and can be effectively decontaminated without damaging the installation equipment in the facility by corrosion. Also, since this liquid droplet does not wet the inside of the facility, it is not necessary to wipe out the liquid. Further, since peracetic acid has a broad antibacterial spectrum, it is possible to kill spore bacteria and the like in a short time by using the apparatus of the invention of JP-B-5969404, and a high decontamination effect can be exhibited.

RELATED ART DOCUMENT

[Patent Document]
[Patent Document 1] JP-B-5969404

SUMMARY OF THE INVENTION

Problem to be Solved by the Invention

However, in the decontamination device according to the above Patent Document 1, the sprayers are started or stopped based on detection values from the temperature-humidity sensors so that the humidities detected by the temperature-humidity sensors can be maintained at a preset humidity. In this case, the sprayed peracetic acid gas starts decomposing within a shorter period of time than decontamination agents such as formaldehyde, hydrogen peroxide and chlorine dioxide, and active oxygen released at the stage of decomposition acts on the SH groups or SS bonds in enzymes in microorganisms and exerts a bactericidal effect by, for example, breaking cell membranes. Also, peracetic acid gas generates acetic acid, oxygen and water when decomposed. Because the humidity is maintained even in this state, simply controlling the sprayers based on the humidity in the decomposition area is insufficient to properly measure the amount of undecomposed peracetic acid in the air sprayed with peracetic acid.

Also, in a decontamination area with high airtightness, the humidity is maintained for a long period of time after peracetic acid gas is sprayed. In addition, the peracetic acid gas decomposes within a short period of time and cannot decontaminate anything after decomposition. In such a case, because no peracetic acid gas can be newly sprayed, time is wasted and effective decontamination cannot be achieved. With the device and method according to Patent Document 1 as described above, sufficient decontamination may not be able to be achieved.

On the other hand, as for the peracetic acid, because it starts decomposing within a short period of time, decontamination has been conventionally carried out only in a high-humidity or supersaturated environment. Also, for effective decontamination in a decontamination space, it is necessary to maintain peracetic acid gas and active oxygen in a rich state. However, in conventional methods, because the humidity is saturated immediately after the release of peracetic acid gas, no peracetic acid gas can be sprayed anymore and a rich state cannot be maintained.

In addition, to use a peracetic acid mixed agent as dry fog, it is necessary to control the concentration of peracetic acid gas strictly by instead controlling humidity because a sensor that measures the concentration of peracetic acid gas has not been developed.

This invention has been made in view of these circumstances, and provides a highly safe and highly effective decontamination device using peracetic acid and a decontamination method employing the decontamination device to solve the above problems.

Means for Solving the Problem

The invention of Claim 1 provides a decontamination device for sterilizing an inside of a facility or an inside of a device installed in the facility in which cells, tissues, culture media, sterile reagents, microorganisms or the like are handled or cultured, including: a dry fog generating machine, installed in a decontamination area, for converting a peracetic acid mixed solution containing low-concentration peracetic acid into dry fog and spraying the dry fog into the decontamination area; a humidity sensor, installed in the above decontamination area, for measuring a humidity in the decontamination area; a gas recovery machine, installed in the above decontamination area, for recovering gas in the decontamination area; and a control device for controlling spraying from the above dry fog generating machine and gas recovery operation by the gas recovery machine based on information from the above humidity sensor, in which a main control and monitoring device, installed outside the above decontamination area, for controlling the control devices of one or more of the above decontamination devices is provided.

The invention of Claim 2 provides a decontamination method for sterilizing an inside of a facility or an inside of a device installed in the facility in which cells, tissues, culture media, sterile reagents, microorganisms or the like are handled or cultured, including: setting in advance a set humidity in a decontamination area; converting a peracetic acid mixed solution containing a low-concentration peracetic acid into dry fog and spraying the dry fog into the decontamination area with a dry fog generating machine; measuring a humidity in the above decontamination area with a humidity sensor; and controlling, with a control device, an operation in which a cycle consisting of start and stop of spraying from the dry fog generating machine and start and stop of gas recovery in the decontamination area by a gas recovery machine is repeated according to a measured humidity from the above humidity sensor so that the above set humidity can be maintained.

The invention of Claim 3 provides the above decontamination method, in which, in the above control device, a spraying ratio, which is the ratio of the period for which the peracetic acid mixed solution is sprayed by the above dry fog generating machine to a decontamination period from a time when the measured humidity in the decontamination area reaches the above set humidity to a time when the operation in which the above cycle is repeated is ended, is controlled at a certain value or higher.

The invention of Claim 4 provides the above decontamination method, in which the operation of the above dry fog generating machine or the above gas recovery machine is controlled by the above control device such that the above dry fog generating machine is stopped and the above gas recovery machine is started when the measured humidity from the above humidity sensor exceeds the above set humidity, and the above gas recovery machine is stopped and the dry fog generating machine is started when the measured humidity from the above humidity sensor falls below the set humidity.

The invention of Claim 5 provides the decontamination method, in which the operation of the above dry fog generating machine or the above gas recovery machine is controlled by the above control device such that the dry fog generating machine is stopped when the measured humidity from the above humidity sensor exceeds the above set humidity and the gas recovery machine is started when a period calculated to increase the spraying ratio to a certain value or higher elapses after the measured humidity exceeds the above set humidity, and the gas recovery machine is stopped and the dry fog generating machine is started when the measured humidity from the above humidity sensor falls below the set humidity.

Effect of the Invention

According to this invention, the humidity is measured, the cycle consisting of start and stop of spraying of peracetic acid dry fog and start and stop of gas recovery is optimized and repeated, and this process is automatically controlled throughout the entire decontamination period so that the ratio of spraying time to the decontamination period, i.e. the spraying ratio, can be equal to or higher than a certain value. Thus, decontamination can be achieved even when the initial humidity is relatively high because the water vapor in the decontamination area is recovered and replaced with fresh peracetic acid gas. As a result, highly effective decontamination can be achieved without being affected by the environment in the decontamination area. This function is an important function especially in high-humidity countries. Also, the decontamination device having these functions can be carried easily, and is therefore adaptable to various places and is easy to use and convenient.

Also, according to this invention, because the gas in the decontamination area is recovered by the gas recovery machine, the decontamination area can be decontaminated at low humidity and under low humidification. Thus, the risk of condensation due to temperature differences in the decontamination area can be significantly reduced, and protective covering which is required in conventional decontamination is unnecessary because even metals that rust easily, such as iron, copper or brass, are not corroded. Also, because decontamination can be achieved at low humidity and under low humidification as described above, ventilation in the decontamination area can be immediately achieved after the completion of the decontamination operation. This contributes to quick recovery of the decontamination area to the original state.

In addition, even in a wide area, by installing a plurality of decontamination devices and controlling the start and stop of spraying and gas recovery by all the dry fog generating machines, a broad decontamination area beyond 2000 m$^3$ can be decontaminated at once.

BRIEF DESCRIPTION OF DRAWINGS

FIG. 2A shows one example of an algorithm used in a decontamination period automatic calculation function of a control device of the decontamination device according to embodiment example 1 of this invention. FIG. 2B is an explanatory view of symbols for the above algorithm.

MODE FOR CARRYING OUT THE INVENTION

Embodiment Example 1

A decontamination device according to embodiment example 1 of this invention is described below. A decontamination device A according to this embodiment example 1 is a device for sterilizing an inside of a sterile manufacturing facility in a pharmaceutical company, a sterile inspection room or a regenerative medicine products manufacturing facility or the like and an inside of a device installed in such a facility in which cells, tissues, culture media, sterile reagents, microorganisms or the like are handled or cultured.

Figure 1:
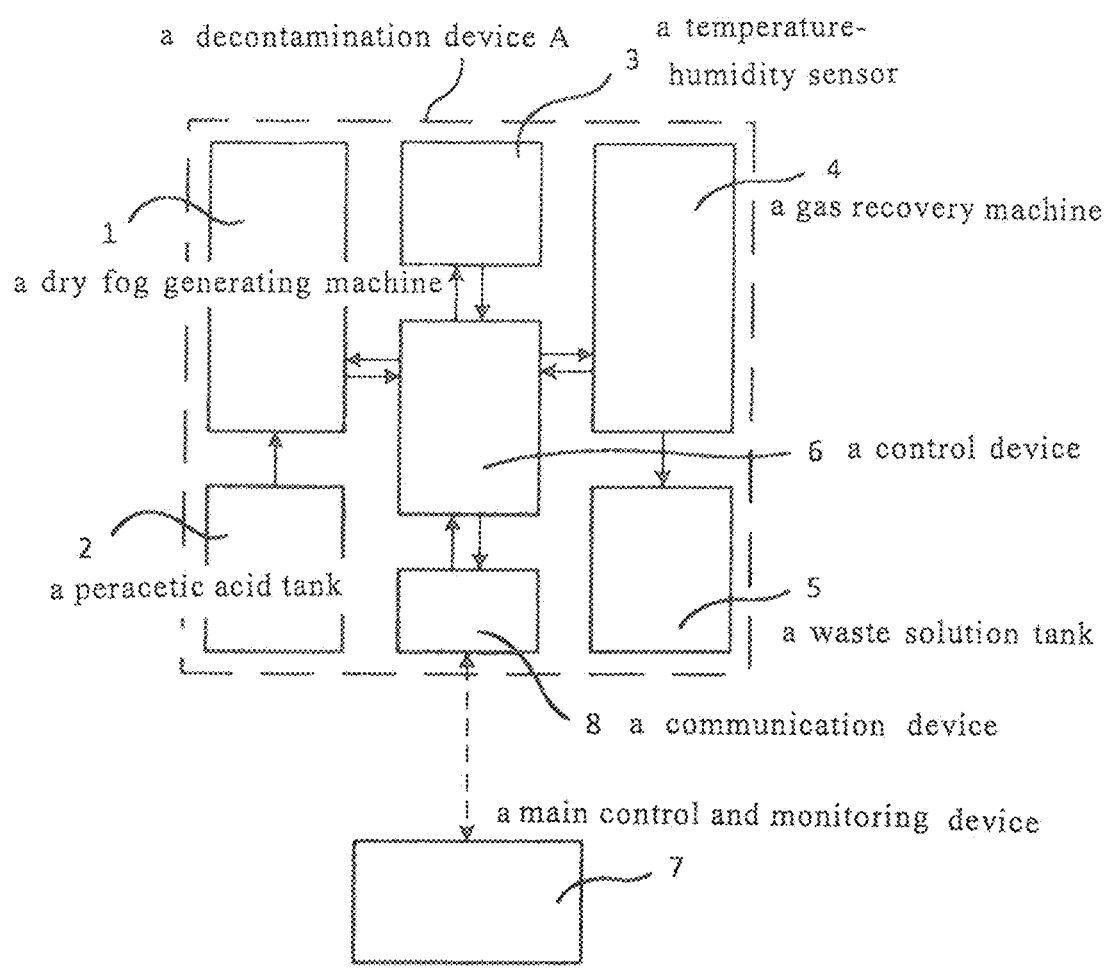
FIG. 1 is a configuration diagram illustrating an outline of a decontamination device according to embodiment example 1 of this invention.

As shown in FIG. 1, the decontamination device A, which is installed in a decontamination area, is constituted of a dry fog generating machine 1, installed in the decontamination area, for converting a peracetic acid mixed solution containing low-concentration peracetic acid into dry fog and spraying the dry fog into the decontamination area, a peracetic acid tank 2 for supplying the above dry fog generating machine 1 with peracetic acid, a temperature-humidity sensor 3, installed in the above decontamination area, for measuring temperature and humidity in the decontamination area, a gas recovery machine 4, installed in the above decontamination area, for recovering gas in the decontamination area, a waste solution tank 5 for storing water from the gas recovered by the above gas recovery machine 4, a control device 6, installed in the above decontamination area, for controlling operation of the dry fog generating machine 1 and the gas recovery machine 4 based on information from the temperature-humidity sensor 3, and a communication device 8 provided integrally with the control device 6. A main control and monitoring device 7, installed outside the above decontamination area, for monitoring and controlling the control device 6 of the above decontamination device A is separately provided.

As the dry fog generating machine 1 used here, an existing dry fog generating machine can be used as long as it can spray a peracetic acid mixed solution in the form of particles with a particle size of 10 μm or smaller as described later. The dry fog generating machine 1 is connected to the control device 6, and starts and stops under the control of the control device 6.

Dry fog usually means fog composed of particles with a particle size of 30 μm or smaller, but it is preferred to control the particle size to 10 μm or smaller for decontamination. Then, it is preferred to convert the particle size into a nano-level by diffusing the medicament sprayed as dry fog with a sufficient volume of air to promote its vaporization. Even dry fog with a particle size of 10 μm or smaller may induce supersaturation to cause condensation when there is a local temperature drop due to temperature variation or temperature change in the decontamination area. To prevent this, it is preferred to carry out decontamination at as low humidity as possible. In addition, it is preferred to rotate the above dry fog generating machine 1 on a rotating table (turn table) to change the spraying direction because spraying in one direction may cause a local increase in humidity in that direction until the humidity is supersaturated to cause condensation.

For the temperature-humidity sensor 3, existing thermometer and hygrometer are used. The temperature-humidity sensor 3 is connected to the control device 6, and transmits detection values of measured temperature, humidity and humidity drop rate to the control device 6. The transmitted detection values are displayed in real time on the control device 6, and these information is recorded automatically. The records (logs) are recorded as a CSV file in a memory, and can be checked and recorded on the main control and monitoring device 7.

In addition, as the gas recovery machine 4, an existing dehumidifier can be used. The gas recovery machine 4 is connected to the control device 6, and starts and stops under the control of the control device 6.

The control device 6 is separately connected electrically to the dry fog generating machine 1, the temperature-humidity sensor 3, and the gas recovery machine 4. The control device 6 starts the dry fog generating machine 1 to spray the medicament. Also, during this decontamination treatment, the control device 6 controls operation of the dry fog generating machine 1 and operation of the gas recovery machine 4 based on detection values from the temperature-humidity sensor 3 so that the humidity detected by the temperature-humidity sensor 3 can be maintained at a preset humidity. In addition, during a decontamination period, this control device 6 measures and records accumulated spraying time of the above dry fog generating machine 1. Also, this control device 6 measures and records accumulated gas recovery time of the above gas recovery machine 4. Also, this control device 6 can receive a set humidity, a decontamination period, a gas recovery period after a decontamination period and so on from the main control and monitoring device 7.

Also, the peracetic acid used here is composed of a mixed solution of peracetic acid, hydrogen peroxide, acetic acid and water (which is hereinafter referred to as "peracetic acid mixed solution"). This peracetic acid mixed solution has a peracetic acid content of 0.01 to 1.2% by weight, a hydrogen peroxide content of 0.06 to 4.8% by weight and an acetic acid content of 0.02 to 6.0% by weight, and the balance is water. This peracetic acid mixed solution is decomposed into acetic acid, oxygen and water after decontamination (reaction), and the acetic acid vaporizes at room temperature without leaving any residue. Specific examples of trade names include Actril (trademark), which is a peracetic acid-based disinfectant.

Also, the main control and monitoring device 7, which controls the control device 6 of the decontamination device A, enables information transmitted from the control device 6 via the communication device 8 of the decontamination device A to be monitored on a monitor, and can control the control device 6 based on this information. These information is accumulated as decontamination logs in the memory.

Also, the communication device 8 has a function of allowing wireless communication between the control device 6 and the main control and monitoring device 7. The above main control and monitoring device 7 can monitor and record the control device 6 of the decontamination device A, temperature and humidity, elapsed time, remaining decontamination period and so on via the communication device 8. Also, the communication device 8 can control the control device 6 according to commands from the main control and monitoring device 7.

Next, a method for decontaminating an inside of a facility and facility equipment in the facility using the decontamination device A, the main control and monitoring device 7 and the communication device 8 according to this embodiment example 1 is described. Here, the following three working steps are carried out. First, temperature, humidity and drop rate of humidity are monitored. Secondly, a cycle consisting of start and stop of spraying of dry fog of a peracetic acid mixed solution and start and stop of recovery thereof is controlled based on the above monitoring, and this cycle is repeated. Thirdly, the above first and second work steps are controlled automatically over the entire decontamination period so that the ratio of spraying time in the decontamination period can be equal to or higher than a certain value. The procedure including the three working steps is referred to as "cyclic decontamination method." Here, the decontamination period means the period from a time when the measured humidity in the decontamination area reaches the above set humidity to a time when the operation in which the above cycle is repeated is ended.

The temperature and humidity in the decontamination area to be decontaminated are measured by the temperature-humidity sensor 3 to determine in advance a set humidity at which supersaturation does not occur. The dry fog generating machine 1 converts the peracetic acid mixed solution into dry fog and sprays the dry fog into the decontamination area. The dry fog is diffused and vaporized with a sufficient volume of air, and spraying of the above peracetic acid mixed solution is stopped when the humidity in the decontamination area reaches the above set humidity. Then, the gas recovery machine 4 is started to recover gas in the decontamination area. During this process, the temperature-humidity sensor 3 continues to measure the temperature, humidity and humidity drop rate in the above decontamination area. Then, when the humidity drops below the set humidity, the recovery is stopped and the above dry fog generating machine 1 starts spraying the peracetic acid mixed solution again to increase the humidity to the set humidity.

A series of actions from a time when spraying is stopped as the measured humidity reaches the set humidity as a result of spraying by the above dry fog generating machine 1 to a time when the humidity reaches again to the set humidity as a result of spraying by the dry fog generating machine 1 after the measured humidity drops below the set humidity as a result of gas recovery by the above gas recovery machine 4 is defined as one cycle. This one cycle takes approximately 5 to 10 minutes. Then, the operation in which the cycle consisting of start and stop of spraying by the dry fog generating machine and start and stop of gas recovery from the inside of the decontamination area by the gas recovery machine is repeated is controlled by the control device 6 according to the measured humidity from the above humidity sensor so that the set humidity can be maintained. The gas recovery machine is started when a set period has elapsed after the set humidity is reached in the first cycle, but optimum timing is simulated based on data of temperature, humidity and humidity drop rate accumulated in the control device 6 and automatic control is performed by a computer in the subsequent cycles. This optimum timing means to control the operation time of gas recovery by calculating a spraying ratio, the ratio of the period for which the peracetic acid mixed solution is sprayed by the above dry fog generating machine to the decontamination period from a time when the measured humidity in the decontamination area reaches the above set humidity to a time when the operation in which the above cycle is repeated is ended, to be a high value equal to or higher than a certain value.

As for the automatic control of the decontamination period, unsuccessful decontamination due to human error by which an extremely short decontamination period is set can be prevented by adding an algorithm to calculate a decontamination period for which 6 logs or more of spore-forming bacteria can be reduced using an initial temperature and an initial humidity in the decontamination area.

In other words, before the decontamination operation is started, a temperature in the decontamination area is measured by the temperature-humidity sensor 3 and the saturated vapor amount at the temperature is calculated. Next, a humidity in the decontamination area is measured. From the measurement value of humidity and the saturated vapor amount obtained as described above, the amount of water vapor in the decontamination area is calculated. By this procedure, it is possible to calculate the amount of peracetic acid disinfectant droplets that can be sprayed into the decontamination area. In addition, from the amount of peracetic acid disinfectant to be sprayed calculated here, a decontamination period from a time when a predetermined humidity to be maintained in a preset decontamination area is reached to a time when the operation in which the above cycle is repeated is ended can be determined based on an algorithm that has been completed in the light of many decontamination condition test results. One example of an algorithm that can be used in the decontamination period automatic calculation function that the control device 6 of this invention has is shown in FIG. 2A, FIG. 2B. The decontamination device A of this invention does not need to spray the disinfectant excessively because it has such a decontamination period automatic calculation function, and can provide a stable decontamination level because it can determine a decontamination period based only on the temperature and humidity in the decontamination area.

Also, as for the above humidity drop, a decrease in humidity in the decontamination area occurs even when protective measures such as adhesive tapes are applied to the exhaust port or door of the decontamination area because there remains a slight airstream between the inside and outside of the decontamination area and the medicament and humidity are carried out of the decontamination area by the airstream.

Next, the effect of this decontamination method was experimented. The decontamination area was a clean room with an area of 38 $m^3$, and the temperature and humidity at the time of experiment were respectively 16.5° C. and 60%, 19.2° C. and 44%, and 17.8° C. and 28% for test No. DH5, test No. DH6 and test No. NDH7, which are described later. Also, in this experiment, dry fog generating machines 1 with a spray amount of 15 to 20 ml/min were used. In addition, here, two dry fog generating machines 1 were used. Also, a gas recovery machine 4 which can recover gas at a rate of 300 to 500 ml/h was used. These dry fog generating machines 1 and the gas recovery machine 4 were controlled by the control device 6. Also, as the temperature-humidity sensor 3, a capacitance-type humidity sensor was used.

Figure 3:
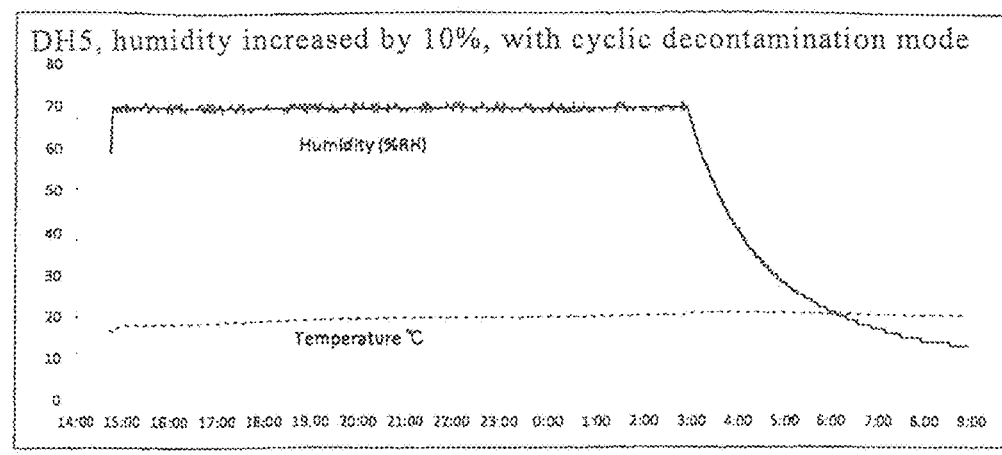
FIG. 3 is a graph chart showing a result of decontamination performed with the humidity increased by 10% humidification with a decontamination method according to embodiment example 1 of this invention.
Figure 4:
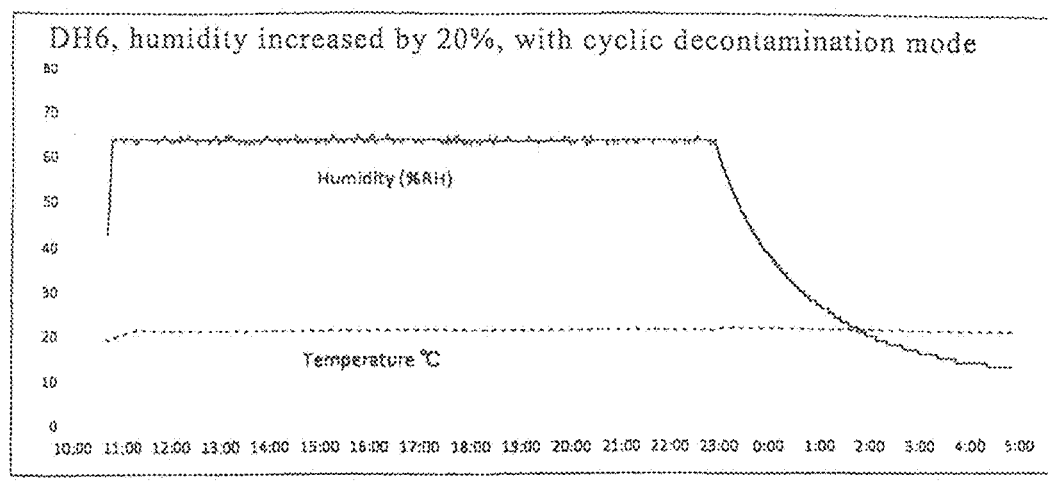
FIG. 4 is a graph chart showing a result of decontamination performed with the humidity increased by 20% with the decontamination method according to embodiment example 1 of this invention.
Figure 5:
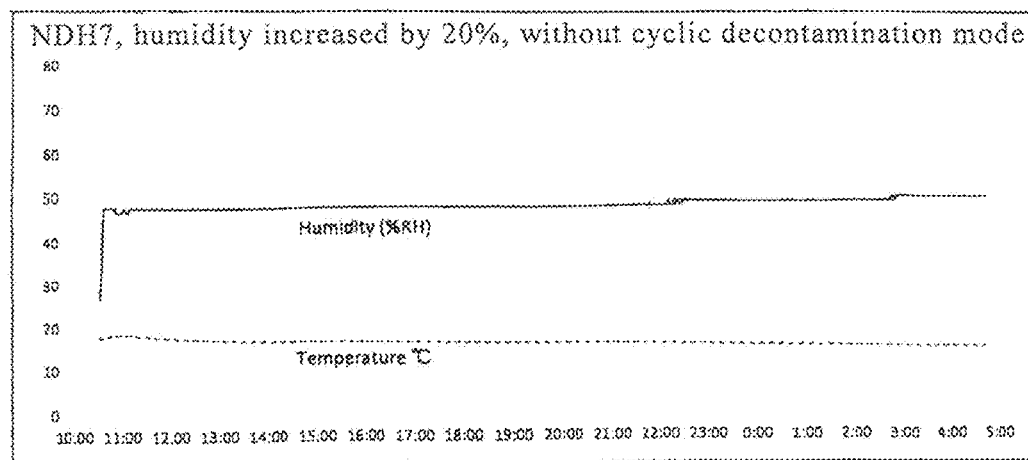
FIG. 5 is a graph chart showing a result of decontamination performed with the humidity increased by 20% with a conventional method instead of the decontamination method according to embodiment example 1 of this invention.
Figure 6:
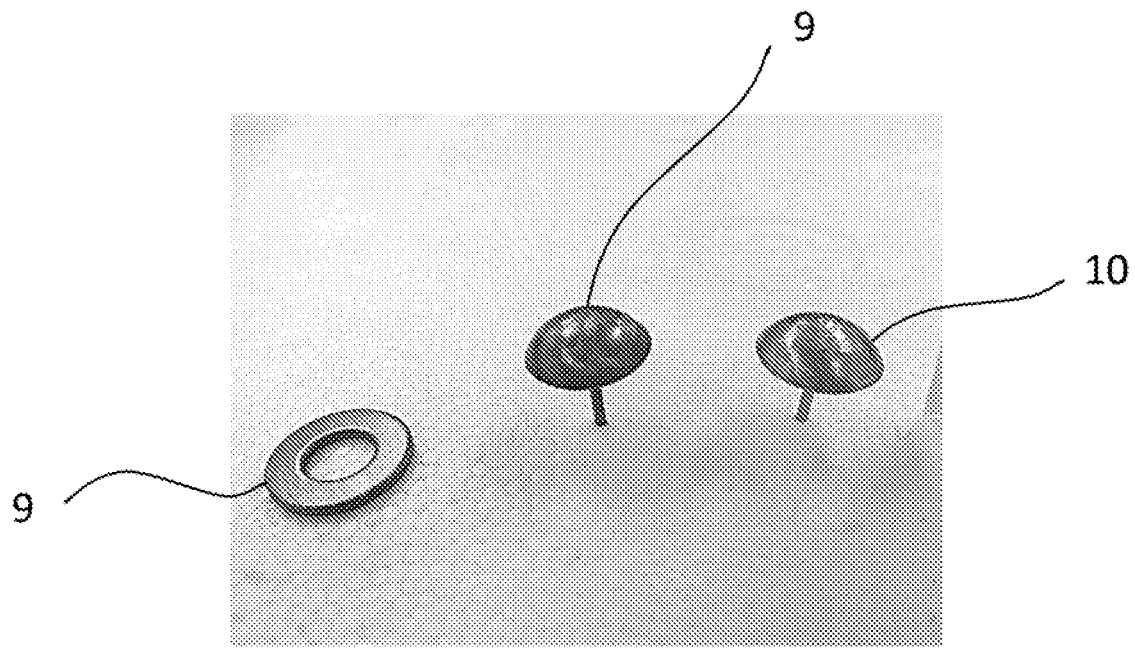
FIG. 6 is a drawing-substitute photograph showing that no green rust was subsequently formed on copper and brass placed in a decontamination area when the decontamination method according embodiment example 1 of this invention was carried out.
Figure 7:
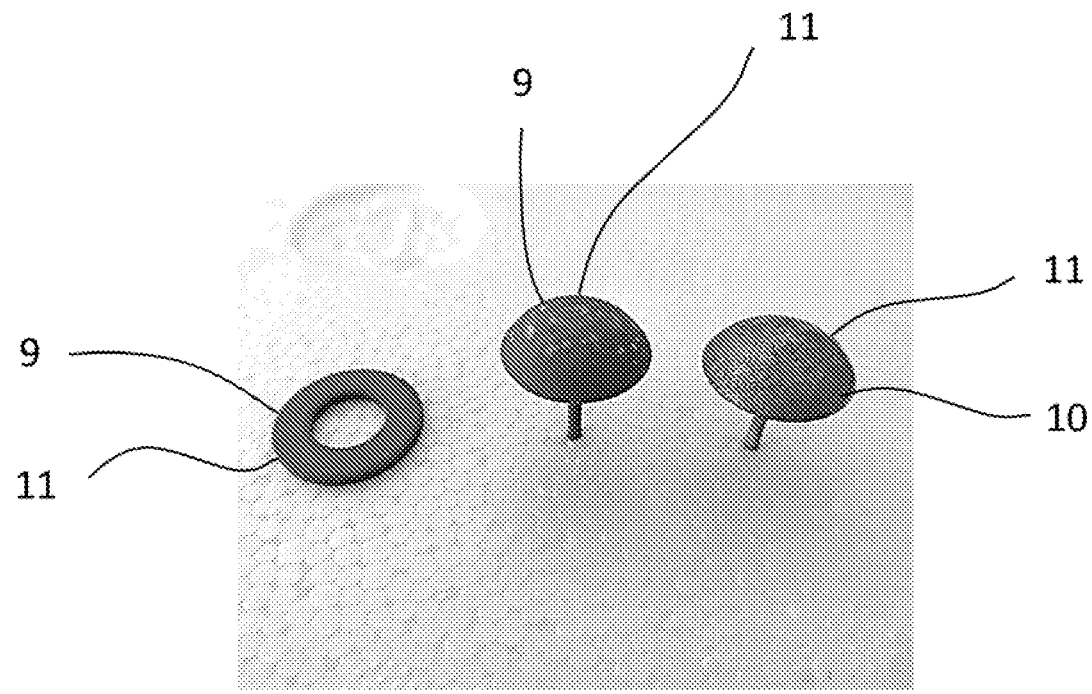
FIG. 7 is a drawing-substitute photograph showing that a green rust film was subsequently formed on copper and brass sprayed with dry fog and placed in a decontamination area as an experiment for comparison with the above FIG. 6.
Figure 8:
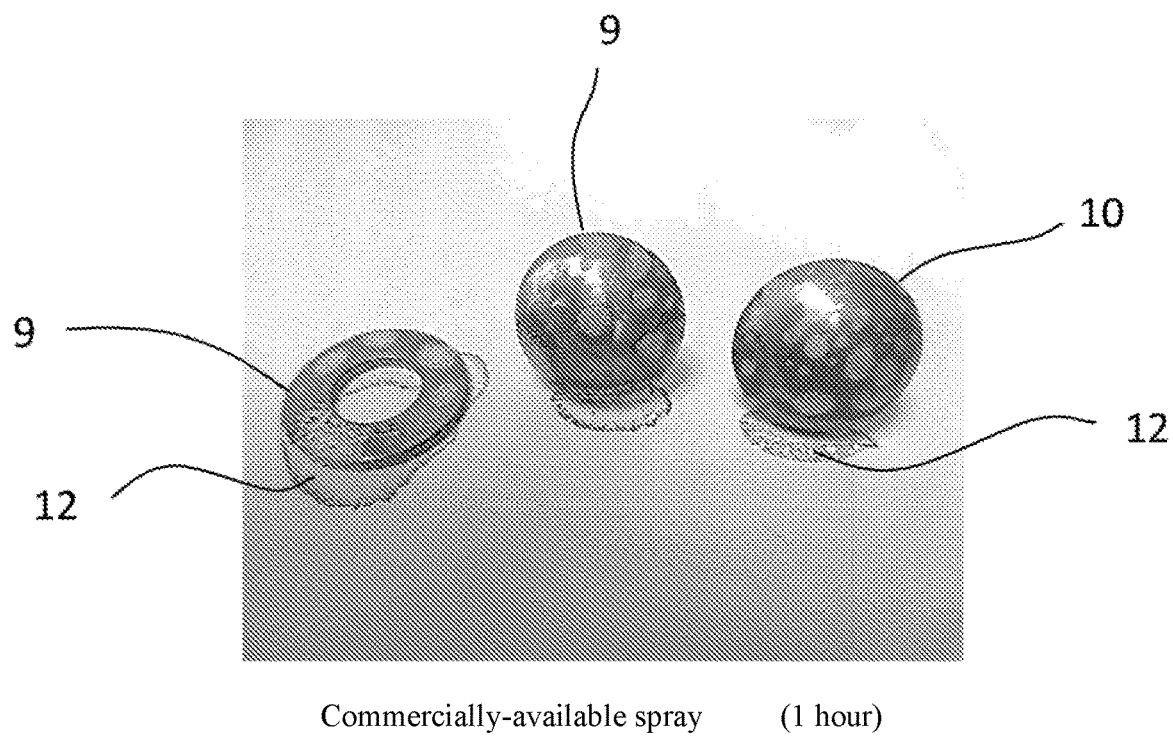
FIG. 8 is a drawing-substitute photograph showing that green rust was subsequently formed on copper and brass sprayed using a commercially-available spray and placed in a decontamination area as an experiment for comparison with the above FIG. 6.

FIG. 3 shows the result obtained when the above cyclic decontamination method was automatically controlled with the humidity increased by 10% from an initial humidity 60%, wherein the vertical axis represents relative humidity (%) and temperature (° C.) and the horizontal axis represents time (The same applies to FIG. 4 and FIG. 5. In Table 1, which is described later, this is denoted as test No. DH5). Here, the experiment was started at about 15:00, and the humidity was immediately increased by 10%. After that, numerous minute changes in humidity were observed till about 3:00 the next day. There changes were due to the above cyclic decontamination method controlled automatically based on humidity drops. The humidity dropped drastically from about 3:00 the next day and fell below 15% at about 9:00. This indicates that decontamination was achieved effectively and medicament recovery was being carried out as a whole after the decontamination was completed at about 3:00. The ratio of the above spraying time in the 12-hour decontamination period in this test No. DH5, i.e., the spraying ratio, was as high as 13.6%.

Next, FIG. 4 shows the result obtained when the above cyclic decontamination method was automatically controlled with the humidity increased by 20% from an initial humidity 44% (denoted as test No. DH6). Here, the experiment was started at about 11:00, and the humidity was immediately increased by 20% from 44% to 64%. After that, very minute changes were observed till about 23:00 in the midnight. These changes were due to the above cyclic decontamination method controlled automatically based on the humidity drops. The humidity dropped drastically from about 23:00 and fell below 15% at about 5:00 the next day. This indicates that decontamination was achieved effectively and medicament recovery was being carried out as a whole after the decontamination was completed at about 23:00. The spraying ratio in the 12-hour decontamination period in this test No. DH6 was as high as 11.7%.

In addition, FIG. 5 shows the result obtained when the humidity in the decontamination area was measured with the temperature-humidity sensor 3 and spraying from the dry fog generating machine 1 was simply started and stopped so that the humidity could reach a set value without using the above cyclic decontamination method with the humidity increased by 20% from an initial humidity 28% (denoted as test No. NDH7). Also, the same dry fog generating machines 1 and the temperature-humidity sensor 3 as those used in the above test No. DH6 were used. Here, the experiment was stated at about 11:00 and the humidity was immediately increased by 20% from 28% to 48%. The decontamination was completed at about 1:00 the next day, but almost no change was observed during the time. This, off course, indicates that no cyclic decontamination was carried out, and the humidity showed almost no change till 4:00 the next day. The spraying ratio in the 12-hour decontamination period of this test No. NDH7 was as low as 1.2%.

The results of the above three experiments are shown in Table 1 below. BIs (biological indicators) were placed "1. On a centrifugal separator," "2. On a central workbench" and "3. At an upper corner of a wall" in the decontaminated area, and the BIs were subsequently collected and cultured to observe the decontamination situation. As a result, all the BIs gave a negative result (decrease in spore-forming bacteria by 6 logs or more) in the above DH5 and DH6, whereas all the BIa gave a positive result in NDH7, which indicates no decontamination was achieved at all. Here, the spore-forming bacterial species cultured to confirm the decontamination situation as described above was *G. stearothermophilus*, which is a heat-resistant bacterium that is regarded as one of the strongest among spore-forming bacteria and an indicator organism for decontamination evaluation in Japanese Pharmacopoeia.

TABLE 1

| Test No. | Increase in humidity | Decontamination humidity | Cyclic decontamination mode | BI installation location and culture result ||| Decontamination period | Amount sprayed | Amount recovered |
| | | | | 1. On centrifugal separator | 2. On central workbench | 3. At upper corner of wall | | | |
| --- | --- | --- | --- | --- | --- | --- | --- | --- | --- |
| DH5 | 10% | 70% | Yes | Negative (−) | Negative (−) | Negative (−) | 12 hours | 2440 ml | 2760 ml |
| DH6 | 20% | 64% | Yes | Negative (−) | Negative (−) | Negative (−) | 12 hours | 2340 ml | 2500 ml |

TABLE 1-continued

| | | | | BI installation location and culture result | | | | | |
|---|---|---|---|---|---|---|---|---|---|
| Test No. | Increase in humidity | Decontamination humidity | Cyclic decontamination mode | 1. On centrifugal separator | 2. On central workbench | 3. At upper corner of wall | Decontamination period | Amount sprayed | Amount recovered |
| NDH7 | 20% | 48% | No | Positive (+) | Positive (+) | Positive (+) | 12 hours | 240 ml | 0 ml |

Also, the amount sprayed and the amount recovered in this Table 1 indicate the amount of dry fog sprayed and the amount of gas recovered, respectively, and are 2,440 ml and 2,760 ml for DH5 and 2,340 ml and 2,500 ml for DH6. This indicates that the disinfectant was sprayed appropriately and the gas was recovered appropriately and that the amount recovered was greater than the amount sprayed in both cases because the existing humidity was recovered in addition to the amount sprayed. This is because this decontamination method is carried out at low humidity and under low humidification. This helps to dry the decontamination area early after decontamination and contributes to early recovery of the decontamination area. On the other hand, in NDH7, the amount sprayed was 240 ml and the amount recovered was zero, and the amount sprayed was approximately 1/10 of those in the above DH5 and DH6. In NDH7, the amount sprayed was extremely small, which indicates that effective decontamination is difficult in a clean room with high airtightness because this is a conventional method in which spraying is carried out after the humidity decreases naturally.

From the above experiment results, it was able to be confirmed that, by automatically controlling the above cycle consisting of start and stop of spraying of dry fog and start and stop of gas recovery so that the spraying ratio, which is the ratio of the period for which the peracetic acid mixed solution is sprayed by the above dry fog generating machine to the decontamination period from a time when the measured humidity in the decontamination area reaches the above set humidity to a time when the operation in which the above cycle is repeated is ended, can be equal to or higher than a certain value, spore-forming bacteria can be reduced by 6 logs or more when the decontamination period is extended to, for example, 12 hours even when the rate of increase from an initial humidity is as low as 10 to 20%. Also, it can be understood from the above experiment results that the spraying ratio higher than a certain value means a spraying ratio equal to or higher than 10% and spore-forming bacteria can be reduced by 6 logs or more at such a spraying ratio. Also, too high a spraying ratio value may lead to a waste of peracetic acid mixed solution. Also, decontamination was achieved at a humidity of 80% or higher or in a supersaturated humidity condition in a conventional decontamination process using peracetic acid mist (dry fog), whereas it was confirmed that spore-forming bacteria can be reduced by 6 logs or more even when the humidity is controlled to 70% or 64% in this decontamination method. Also, even when the initial humidity in the decontamination area is relatively high, decontamination can be achieved because the water vapor in the decontamination area is recovered and replaced by fresh peracetic acid gas when the above three working steps are carried out. In view of these facts, the decontamination method according to this embodiment example 1 can be regarded as a low-humidity and low-humidification decontamination method.

Next, a metal corrosivity exposure test by the low-humidity and low-humidification decontamination method according to this embodiment example 1 was conducted. For comparison, a test using a commercially available spray as a device for spraying the peracetic acid mixed solution (denoted as "commercially-available spray" in Table 2) and a test using conventional dry fog (dry fog was produced by ultrasonic waves and the set humidity was set to 95% or higher so that the dry fog mist did not vaporize easily and could contact the metal) were conducted. The experiments were conducted in the same place as where the effect of the above decontamination method was experimented. As shown in Table 2 and FIG. 6, the results were as follows. There was no effect observed on metals of copper 9 and brass 10, which are most vulnerable to corrosion, placed in the decontamination area in the case of the decontamination method according to embodiment example 1 (denoted as "cyclic decontamination method" in Table 2). On the other hand, as shown in Table 2 and FIG. 7, a green rust film 11 was observed on the metal pieces exposed to the dry fog, and, as shown in Table 2 and FIG. 8, green rust 12 and acetic acid salt (copper acetate) were observed on copper 9 and brass 10, respectively, sprayed with the medicament using the commercially-available spray. These results indicate that metal corrosion cannot be prevented by the commercially-available spray and that metal corrosion cannot be prevented even with the conventional dry fog as the green rust film 11 was observed. On the other hand, it was also proved that the decontamination method according to this embodiment example 1, which can be carried out at low humidity and under low humidification, causes no problem in terms of metal corrosion.

TABLE 2

| Test No. | Exposure method | Observation period | Changes observed: Copper | Changes observed: Brass |
|---|---|---|---|---|
| 1 | Commercially-available spray | 1 hour | Green rust | Green rust |
| 2 | Dry fog | 1 hour | Green rust film | Green rust film |
| 3 | Cyclic decontamination method | 12 hours | No change | No change |

As for the airtightness in the decontamination area, it is necessary to strictly control the humidity so that electronic machines and devices cannot be corroded or broken by condensation water of peracetic acid. When the gas concentration (humidity) is strictly controlled, peracetic acid mist cannot be sprayed any more after the set humidity is reached in a decontamination area with high airtightness. In such a case, it is possible to ensure successful decontamination without being affected by the degree of airtightness in the decontamination area by simultaneously activating the above cyclic decontamination function, in which a mixed gas of peracetic acid gas and acetic acid gas is recovered and fresh peracetic acid gas is sprayed, and a function in which a decontamination period is calculated automatically based on the initial temperature and the initial humidity.

When the decontamination area is large or consists of a plurality of rooms and corridors, a supersaturated state is formed in some space and the medicament condenses into dew when a large amount of peracetic acid mist is generated from one spot. Accordingly, a phenomenon occurs in which the medicament lacks and does not spread into every corner. Neglecting this phenomenon leads to corrosion and improper decontamination. To avoid these, when a large area is decontaminated, a plurality of decontamination devices A is installed in the decontamination area to spray the peracetic acid mist from a plurality of points.

Embodiment Example 2

Figure 9:
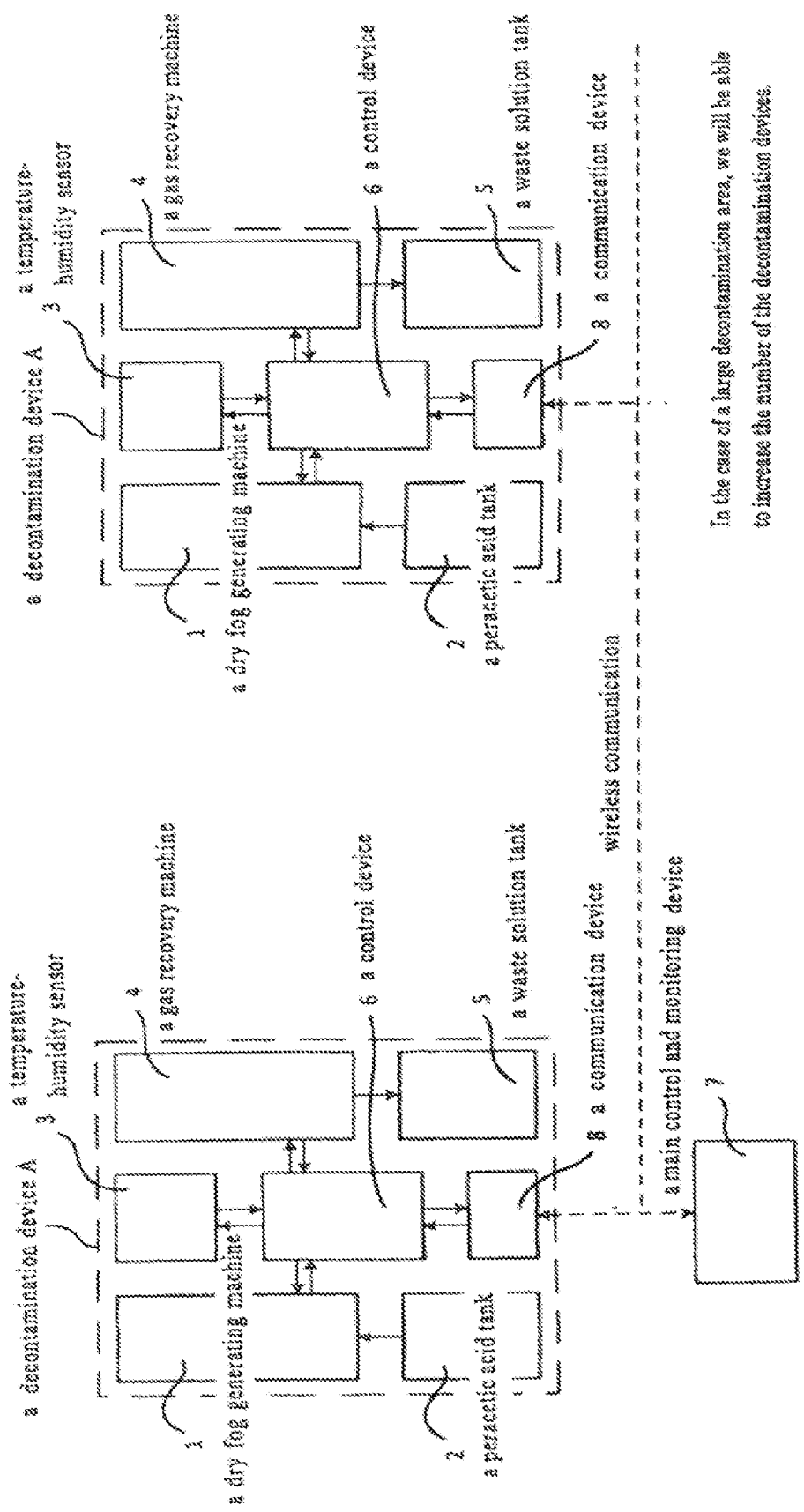
FIG. 9 is a configuration diagram illustrating an outline of a state where a plurality of decontamination devices according to embodiment example 1 of this invention is arranged.

Embodiment example 2 of this invention is described below. Again in this case, as shown in FIG. 9, one main control and monitoring device 7 for controlling the control device 6 of each decontamination device A is installed at a location remote from the decontamination area. This main control and monitoring device 7 can monitor and control information transmitted from each control device 6 via each communication device 8 of the plurality of decontamination devices A. All the basic configuration is the same as that of the above embodiment example 1.

Each of the plurality of decontamination devices A wirelessly communicates with the other decontamination devices A, and needs to have a function of maintaining the humidity in the space corresponding to each decontamination device A so that the humidity cannot be escaped when the other decontamination devices A have not completed decontamination. The operator can simultaneously command all the dry fog generating machines 1 to start and stop spraying and the gas recovery machines 4 to start and stop gas recovery wirelessly from the main control and monitoring device 7. With this method, a large decontamination area greater than 2000 m³ can be decontaminated at once.

Also, as described above, each communication device 8 has a function of wirelessly communicating with the main control and monitoring device 7. Because each decontamination device A has such a communication function, the decontamination devices A can have a function of automatically adjusting their decontamination end times to coincide with each other. Also, the control devices 6 of all the decontamination devices A can be controlled by a command from the main control and monitoring device 7.

Also, because each communication device 8 of individual decontamination devices A and the communication devices 8 of the other decontamination devices A are mutually connected, the decontamination devices A that reach the set humidity earlier usually end decontamination earlier. Then, the amount of peracetic acid mixed solution sprayed in the entire decontamination device decreases. Thus, it is possible to adjust the decontamination end times of the decontamination devices A to coincide with that of the decontamination device A with the latest end time using the function of automatically adjusting the decontamination end times to coincide with each other so as to avoid formation of areas that cannot be decontaminated. For example, when the humidity in a room in the facility that is smaller than the others increases earlier than those in the other places, a humidity suitable for decontamination at which condensation does not occur is maintained based on measured humidity information from the temperature-humidity sensor 3 connected to the control device 6 of the decontamination device A. Then, the decontamination devices A that have reached the humidity suitable for decontamination maintained the humidity in sequence. Until the end of the decontamination period of the decontamination device A that reaches the proper humidity last, the decontamination periods of the other decontamination devices A can be automatically extended in order to prevent each decontamination device A from ending decontamination earlier and causing the humidity to fall below the set humidity.

As for the target decontamination area, when this cyclic decontamination method is used, it is possible to decontaminate not only a large room but also a small space in a device such as incubator, clean bench, safety cabinet, pass box, refrigerator or centrifuge by simply installing and operating a downsized integrated unit including a dry fog generating machine 1 for converting peracetic acid mixed solution containing low-concentration peracetic acid into dry fog and spraying the dry fog, a peracetic acid tank 2 for supplying the dry fog generating machine 1 with peracetic acid, a temperature-humidity sensor 3 for measuring temperature and humidity in the device, a gas recovery machine 4 for recovering gas in the device, a waste solution tank 5 for storing water from the gas recovered by the above gas recovery machine 4, a control device 6 for controlling operation of the dry fog generating machine 1 and the gas recovery machine 4 based on information from the temperature-humidity sensor 3 and a communication device 8 provided integrally with the control device 6 when decontamination is carried out. Decontamination can be also achieved in a device that originally has no decontamination function. It is certainly possible to use the cyclic decontamination method not only in an integrated or separate type unit but also in a unit incorporated in the device. Also, devices and machines placed in the decontamination area can be simultaneously decontaminated. So far, devices that cannot be taken out for maintenance because there is no way to decontaminate them cannot be used in a biohazard room. Because this decontamination method can achieve decontamination without breaking electronic components and devices, it can be used as a new decontamination method. This increases devices that can be taken into a biohazard room, and leads to more effective research on pathogenic microorganisms and development of therapeutic agents.

As for odor, in conventional space decontamination using peracetic acid, things get wet everywhere because decontamination is generally carried out in a supersaturated state. In particular, when the wall side of an installed device or the floor gets wet, wiping work cannot be performed and the odor does not disappear until it dries. The risk of getting wet can be eliminated when decontamination is carried out in a dry state from the beginning to the end as in this cyclic decontamination method (in which the degree of humidification is too low to cause things to get wet). However, because acetic acid gas remains in a high humidity state after the completion of decontamination, the inside of the building will be filled with the odor of acetic acid unless an exhaust duct to the outside is installed when the air conditioner in the room is operated for evacuation. To avoid such a situation, it is preferred to recover the acetic acid gas in the decontamination area with the gas recovery machine 4.

As described above, a conventional decontamination method using peracetic acid has advantages of being able to decontaminate microorganisms such as bacteria and fungi including virus and spore-forming bacteria and being safe to humans, but the strong metal corrosivity and acetic acid odor still remain as big issues. However, by using the new decontamination method that uses a low-concentration peracetic acid mixed solution and the dry fog generating machine 1, the gas recovery machine 4, the temperature-humidity sensor 3 and the main control and monitoring device 7, which realizes the decontamination method, the problems, corrosion of electronic machines and devices and acetic acid odor after decontamination, can be solved. In addition, because various devices installed in the decontamination area can be decontaminated without any protection, the problem left unsolved as a contamination source so far can be also solved almost entirely. Also, because decontamination is carried out in a dry state from the beginning to the end, there is no need for neutralization, evacuation and wiping after decontamination. In addition, it has been confirmed that spore-forming bacteria can be reduced by 6 log or more both in decontamination of an inside of a device and in decontamination of a room, and it has been proved that a sufficient decontamination effect can be achieved.

While temperature, humidity and humidity drop rate are measured with the temperature-humidity sensor 3 in this embodiment example 1, the start and end of spraying from the dry fog generating machine 1 and the start and end of the recovery operation of the gas recovery machine 4 in the decontamination device A may be determined based only on measurement of humidity. Also, the start of the recovery operation of the gas recovery machine 4 of the decontamination device A may be determined based on the period from a time when the measured humidity reaches the set humidity as a result of gas spraying from the dry fog generating machine 1.

Also, while a device consisting of the dry fog generating machine 1, the peracetic acid tank 2, the temperature-humidity sensor 3, the gas recovery machine 4, the waste solution tank 5, the control device 6 and the communication device 8 is shown as the decontamination device A, these may be integrated into one unit, separated from each other or incorporated into the target device irrespective of whether the decontamination area is in a facility or in a device.

Also, while two dry fog generating machines 1 are used in the above decontamination device A shown in FIG. 1 in the experiment of the effect of the decontamination method, FIG. 1 shows a basic configuration of the decontamination device A and the numbers of the dry fog generating machines 1, the temperature-humidity sensors 3, the gas recovery machines 4 and so on can be selected as appropriate based on the situation of the decontamination area.

DESCRIPTION OF REFERENCE NUMERALS AND SYMBOLS

A: decontamination device
1: dry fog generating machine
2: peracetic acid tank
3: temperature-humidity sensor
4: gas recovery machine
5: waste solution tank
6: control device
7: main control and monitoring device
8: communication device

The invention claimed is:

1. A decontamination method for sterilizing an inside of a facility, or an inside of a device installed in the facility, in which cells, tissues, culture media, sterile reagents, microorganisms or the like are handled or cultured, comprising:
setting in advance a set humidity in a decontamination area at which supersaturation to cause condensation does not occur;
generating dry fog by converting a peracetic acid mixed solution containing a low-concentration peracetic acid into the dry fog in a form of particles with a particle size of 10 μm or smaller and spraying the dry fog into the decontamination area;
measuring a humidity in the decontamination area with a humidity sensor; and
controlling, an operation comprising repeating a cycle consisting of start and stop of spraying the dry fog and start and stop of gas recovery in the decontamination area according to a measured humidity from the humidity sensor so that the set humidity can be maintained,
wherein a sprayed peracetic acid gas contained in the dry fog starts decomposing in the decontamination area to generate acetic acid, oxygen and water, and active oxygen released during the decomposition acts on SH groups or SS bonds in enzymes in microorganisms and exerts a bactericidal effect, wherein the spraying of the dry fog containing the peracetic acid mixed solution is stopped when the humidity in the decontamination area reaches the set humidity;
wherein, after the spraying of the dry fog containing the peracetic acid mixed solution is stopped, the gas recovery of gas in the decontamination area by a gas recovery machine recovers water vapor and the acetic acid and to reduce humidity in the decontamination area, when the humidity in the decontamination area drops below the set humidity the gas recovery by the gas recovery machine is stopped and fresh peracetic acid mixed solution as dry fog is sprayed in the decontamination area to thereby replace the water vapor removed by the gas recovery with the fresh peracetic acid mixed solution in the decontamination area, wherein the active oxygen is generated repeatedly by repeat of the spraying of the dry fog and the gas recovery.

2. The decontamination method according to claim 1, wherein a spraying ratio is equal to or higher than 10%, wherein the spraying ratio is the ratio of (a) a time period that the peracetic acid mixed solution is sprayed as the dry fog to (b) a decontamination time period from a time when the measured humidity in the decontamination area reaches the set humidity to a time when the operation is ended.

3. The decontamination method according to claim 2, wherein the start and stop of the dry fog generating or the gas recovery is controlled such that the dry fog generating is stopped when the measured humidity from the humidity sensor exceeds the set humidity and the gas recovery is started when a period calculated to increase the spraying ratio to a predetermined set value or higher elapses after the measured humidity exceeds the set humidity, and the gas recovery is stopped and the dry fog generating is started when the measured humidity from the humidity sensor falls below the set humidity.

4. The decontamination method according to claim 1, wherein the repeat of the spraying of the dry fog and the gas recovery consequently maintains the active oxygen in a rich state in the decontamination area.

5. A decontamination method for sterilizing an inside of a facility or an inside of a device installed in a facility in which cells, tissues, culture media, sterile reagents, microorganisms or the like are handled or cultured, comprising:
setting in advance a set humidity in a decontamination area at which supersaturation to cause condensation does not occur;
converting a peracetic acid mixed solution containing a low-concentration peracetic acid into dry fog and spraying the dry fog into the decontamination area with a dry fog generating machine, wherein the dry fog generating machine is capable of spraying the peracetic acid mixed solution in a form of particles with a particle size of 10 μm or smaller by blowing air to release the particles as liquid droplets, wherein the dry fog is diffused and vaporized with air;

measuring a humidity in the decontamination area with a humidity sensor; and controlling, with a control device comprising a computer, the control device electrically connected to the dry fog generating machine, an operation comprising repeating a cycle consisting of start and stop of spraying from the dry fog generating machine and start and stop of gas recovery in the decontamination area by a gas recovery machine comprising a dehumidifier according to a measured humidity from the humidity sensor so that the set humidity can be maintained, wherein a sprayed peracetic acid gas contained in the dry fog starts decomposing in the decontamination area to generate acetic acid, oxygen and water, and active oxygen released during the decomposition acts on SH groups or SS bonds in enzymes in microorganisms and exerts a bactericidal effect, wherein the spraying of the dry fog containing the peracetic acid mixed solution is stopped when the humidity in the decontamination area reaches the set humidity;

wherein, after the spraying of the dry fog containing the peracetic acid mixed solution is stopped, the gas recovery of gas in the decontamination area by the gas recovery machine recovers water vapor and the acetic acid and to reduce humidity in the decontamination area, when the humidity in the decontamination area drops below the set humidity the gas recovery by the gas recovery machine is stopped and the dry fog generating machine again sprays fresh peracetic acid mixed solution in the decontamination area as dry fog to thereby replace the water vapor removed by the gas recovery with the fresh peracetic acid mixed solution in the decontamination area, wherein the active oxygen is generated repeatedly by repeat of the spraying of the dry fog and the gas recovery.

6. The decontamination method according to claim 5, wherein, in the control device, a spraying ratio, which is the ratio of (a) the time period that the peracetic acid mixed solution is sprayed by the dry fog generating machine to (b) a decontamination time period from a time when the measured humidity in the decontamination area reaches the set humidity to a time when the operation is ended, is equal to or higher than 10%.

7. The decontamination method according to claim 6, wherein the operation of the dry fog generating machine or the gas recovery machine is controlled by the control device such that the dry fog generating machine is stopped when the measured humidity from the humidity sensor exceeds the set humidity and the gas recovery machine is started when a period calculated to increase the spraying ratio to a predetermined set value or higher elapses after the measured humidity exceeds the set humidity, and the gas recovery machine is stopped and the dry fog generating machine is started when the measured humidity from the humidity sensor falls below the set humidity.

8. The decontamination method according to claim 5, wherein the repeat of the spraying of the dry fog and the gas recovery consequently maintains the active oxygen in a rich state in the decontamination area.

\* \* \* \* \*